US008472688B2

(12) United States Patent
Samsonov et al.

(10) Patent No.: US 8,472,688 B2
(45) Date of Patent: *Jun. 25, 2013

(54) METHOD FOR IMAGE RECONSTRUCTION EMPLOYING SPARSITY-CONSTRAINED ITERATIVE CORRECTION

(75) Inventors: Alexey A. Samsonov, Madison, WI (US); Huimin Wu, Madison, WI (US); Walter F. Block, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1316 days.

This patent is subject to a terminal disclaimer.

(21) Appl. No.: 12/104,924

(22) Filed: Apr. 17, 2008

(65) Prior Publication Data

US 2009/0262996 A1    Oct. 22, 2009

(51) Int. Cl.
*A61B 6/03*    (2006.01)
(52) U.S. Cl.
USPC .......................................... 382/130; 382/131
(58) Field of Classification Search
USPC .......................... 324/300–322; 382/128–132
See application file for complete search history.

(56) References Cited

U.S. PATENT DOCUMENTS

| 4,878,169 | A | 10/1989 | Toner et al. | |
| 8,229,199 | B2 * | 7/2012 | Chen et al. | 382/130 |
| 2007/0010731 | A1 * | 1/2007 | Mistretta | 600/407 |
| 2009/0175523 | A1 * | 7/2009 | Chen et al. | 382/130 |

FOREIGN PATENT DOCUMENTS

| WO | 2009082736 A1 | 2/2009 |
| WO | 2009091824 A1 | 7/2009 |

OTHER PUBLICATIONS

Samsonov et al., HYPRIT: Generalized HYPR Reconstruction by Iterative Estimation, Feb. 2007, ISMRM workshop on Non-Cartesian Imaging.*
Kim et al., An Efficient Method for Compressed Sensing, Sep. 19, 2007, IEEE Conference on Image Processing, 2007, ICIP 2007, pp. III-117 to III-120.*
Johnson et al., Improved Waveform Fidelity using local HYPR Reconstruction (HYPR LR), Published on line Feb. 27, 2008, Magnetic Resonance in Medicine, vol. 59, Issue 3, pp. 456-462.*
Block et al., "Iterative Image reconstruction of Undersampled Radial MRI Data from Multiple Coils", Feb. 2007, ISMRM workshop on Non-Cartesian Imaging.*
A Wiki Call for Papers, ISMRM 2008: International Society for Magnetic Resonance Imaging in Medicine call for papers, available at http://www.wikicfp.com/cfp/servlet/event.showcfp?eventid=1107&copyownerid=100.*
Kathryn L Garden et al; 3-D Reconstruction of the Heart From Few Projections: A Practical Implementation of the McKinnon-Bates Algorithm; IEEE Transactions on Medical Imaging, vol. MI-5, No. 4, Dec. 1986.

(Continued)

*Primary Examiner* — Toan Ton
*Assistant Examiner* — John Corbett
(74) *Attorney, Agent, or Firm* — Quarles & Brady, LLP

(57) ABSTRACT

An image reconstruction method applicable to a number of different imaging modalities including magnetic resonance imaging (MRI), x-ray computed tomography (CT), positron emission tomography (PET), and single photon emission computed tomography (SPECT) is disclosed. A sparsifying image is reconstructed from a series of acquired undersampled data to provide a priori knowledge of a subject being imaged. An iterative reconstruction process is further employed to iteratively determine a correction image for a given image frame that, when subtracted from the sparsifying image, produces a quality image for the image frame.

23 Claims, 11 Drawing Sheets

OTHER PUBLICATIONS

Graeme C McKinnon et al; Towards Imaging the Beating Heart Usefully With A Conventional CT Scanner; IEEE Transactions on Biomedical Engineering, vol. BME-28, No. 2, Feb. 1981.

Irina F Gorodnitsky et al; Sparse Signal Reconstruction From Limited Data Using FOUCSS: A Re-Weighted Minimum Norm Algorithm, IEEE Transactions on Signal Processing, vol. 45, No. 3, Mar. 1997, pp. 600-616.

Jong Chul Ye et al; Projection Reconstruction MR Imaging Using FOCUSS; Magnetic Resonance in Medicine 57:764-775 (2007).

Steffen Weiss et al; Projection-Reconstruction Reduces FOV Imaging; Magnetic Resonance Imaging, vol. 17, No. 4, pp. 517-515, 1999.

Hong Jung et al; Improved k-t BLAST and k-t SENSE using FOCUSS; Physics in Medicine and Biology; IOP Publishing; Phys. Med. Biol. 52 (2007) 3201-3226.

Guang-Hong Chen et al; Prior Image Constrained Compressed Sensing (PICCS): A Method to Accurately Reconstruct Dynamic CT Images From Highly Undersampled Projection Data Sets; Med. Phys. 35 (2), Feb. 2008; 660-663.

URS Gamper et al; Compressed Sensing in Dynamic MRI; Mag. Reson. In Medicine 59:365-373 (2008).

Michael Lustig et al; Compressed Sensing MRI; IEEE Signal Processing Magazine; 72-82.

David L. Donoho; IEEE Transactions On Information Theory, vol. 52, No. 4, Apr. 2006; 1289-1306.

Brendt Wohlberg et al; An Iteratively Reweighted Norm Algorithm for Minimization of Total Variation Functionals; IEEE Signal Processing Letters, vol. 14, No. Dec. 12, 2007; 948-951.

Jiayu Song et al; Sparseness Prior Based Iterative Image Reconstruction for Retrospectively Gated Cardiac Micro-CT; Med. Phys. 34 (11), Nov. 2007; 4476-4483.

Kevin M Johnson et al; Improved Waveform Fidelity Using Local HYPR Reconstruction (HYPR LR); Mag. Reson. In Med. 59:456-462 (2008).

Irina F Gorodnitsky, et al; Sparse Signal Reconstruction From Limited Data Using FOCUSS: A Re-Weighted Minimum Norm Algorithm; IEEE Transactions on Signal Processing; vol. 45, No. 3, Mar. 1993.

Klass P Pruessmann, et al; Advances in Sensitivity Encoding With Arbitrary k-Space Trajectories; Mag. Reson. In Medicine 46:638-651 (2001).

International Search Report; PCT/US2009/040181; 5 pages.

* cited by examiner

METHOD FOR IMAGE RECONSTRUCTION EMPLOYING SPARSITY-CONSTRAINED ITERATIVE CORRECTION

STATEMENT REGARDING FEDERALLY SPONSORED RESEARCH

This invention was made with government support under CA116380 awarded by the National Institutes of Health. The government has certain rights in the invention.

BACKGROUND OF THE INVENTION

The field of the invention is medical imaging and particularly, methods for reconstructing images from acquired image data.

Magnetic resonance imaging (MRI) uses the nuclear magnetic resonance (NMR) phenomenon to produce images. When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins, and after the excitation signal $B_1$ is terminated, this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. Each measurement is referred to in the art as a "view" and the number of views determines the quality of the image. The resulting set of received NMR signals, or views, or k-space samples, are digitized and processed to reconstruct the image using one of many well known reconstruction techniques. The total scan time is determined in part by the length of each measurement cycle, or "pulse sequence", and in part by the number of measurement cycles, or views, that are acquired for an image. There are many clinical applications where total scan time for an image of prescribed resolution and SNR is a premium, and as a result, many improvements have been made with this objective in mind.

Projection reconstruction methods have been known since the inception of magnetic resonance imaging and this method is again being used as disclosed in U.S. Pat. No. 6,487,435. Rather than sampling k-space in a rectilinear, or Cartesian, scan pattern as is done in Fourier imaging and shown in FIG. 1, projection reconstruction methods sample k-space with a series of views that sample radial lines extending outward from the center of k-space as shown in FIG. 2. The number of views needed to sample k-space determines the length of the scan and if an insufficient number of views are acquired, streak artifacts are produced in the reconstructed image. The technique disclosed in U.S. Pat. No. 6,487,435 reduces such streaking by acquiring successive undersampled images with interleaved views and sharing peripheral k-space data between successive image frames.

Depending on the technique used, many MR scans currently used to produce medical images require many minutes to acquire the necessary data. The reduction of this scan time is an important consideration, since reduced scan time increases patient throughout, improves patient comfort, and improves image quality by reducing motion artifacts. Many different strategies have been developed to shorten the scan time.

One such strategy is referred to generally as "parallel imaging". Parallel imaging techniques use spatial information from arrays of RF receiver coils to substitute for the encoding that would otherwise have to be obtained in a sequential fashion using RF pulses and field gradients (such as phase and frequency encoding). Each of the spatially independent receiver coils of the array carries certain spatial information and has a different sensitivity profile. This information is utilized in order to achieve a complete location encoding of the received MR signals by a combination of the simultaneously acquired data received from the separate coils. Specifically, parallel imaging techniques undersample k-space by reducing the number of acquired phase-encoded k-space sampling lines while keeping the maximal extent covered in k-space fixed. The combination of the separate MR signals produced by the separate receiver coils enables a reduction of the acquisition time required for an image (in comparison to conventional k-space data acquisition) by a factor that in the most favorable case equals the number of the receiver coils. Thus the use of multiple receiver coils acts to multiply imaging speed, without increasing gradient switching rates or RF power.

Two categories of such parallel imaging techniques that have been developed and applied to in vivo imaging are SENSE (SENSitivity Encoding) and SMASH (SiMultaneous Acquisition of Spatial Harmonics). With SENSE, the undersampled k-space data is first Fourier transformed to produce an aliased image from each coil, and then the aliased image signals are unfolded by a linear transformation of the superimposed pixel values. With SMASH, the omitted k-space lines are filled in or reconstructed prior to Fourier transformation, by constructing a weighted combination of neighboring lines acquired by the different receiver coils. SMASH requires that the spatial sensitivity of the coils be determined, and one way to do so is by "autocalibration" that entails the use of variable density k-space sampling.

A more recent advance to SMASH techniques using autocalibration is a technique known as GRAPPA (GeneRalized Autocalibrating Partially Parallel Acquisitions), introduced by Griswold et al. This technique is described in U.S. Pat. No. 6,841,998 as well as in the article titled "Generalized Autocalibrating Partially Parallel Acquisitions (GRAPPA)," by Griswold et al. and published in *Magnetic Resonance in Medicine* 47:1202-1210 (2002). Using these GRAPPA techniques, lines near the center of k-space are sampled at the Nyquist frequency (in comparison to the greater spaced lines at the edges of k-space). These so-called autocalibration signal (ACS) lines are then used to determine the weighting factors that are used to reconstruct the missing k-space lines. In particular, a linear combination of individual coil data is used to create the missing lines of k-space. The coefficients for the combination are determined by fitting the acquired data to the more highly sampled data near the center of k-space.

In a computed tomography ("CT") system, an x-ray source projects a fan-shaped beam which is collimated to lie within an X-Y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile".

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object.

As with MRI, there are a number of clinical applications for x-ray CT where scan time is at a premium. In time-resolved angiography, for example, a series of image frames are acquired as contrast agent flows into the region of interest. Each image is acquired as rapidly as possible to obtain a snapshot that depicts the inflow of contrast. This clinical application is particularly challenging when imaging coronary arteries or other vessels that require cardiac gating to suppress motion artifacts.

There are two methods used to reconstruct images from an acquired set of projection views as described, for example, in U.S. Pat. No. 6,710,686. In MRI the most common method is to regrid the k-space samples from their locations on the radial sampling trajectories to a Cartesian grid. The image is then reconstructed by performing a 2D or 3D Fourier transformation of the regridded k-space samples. The second method for reconstructing an MR image is to transform the radial k-space projection views to Radon space by first Fourier transforming each projection view. An image is reconstructed from these signal projections by filtering and back-projecting them into the field of view (FOV). As is well known in the art, if the acquired signal projections are insufficient in number to satisfy the Nyquist sampling theorem, streak artifacts are produced in the reconstructed image.

A new image reconstruction method called HighlY constrained backPRojection (HYPR) has been developed. As described in co-pending U.S. patent application Ser. No. 11/482,372, HYPR provides a method in which quality images can be produced with far fewer projection signal profiles when a priori knowledge of the signal information is used in the reconstruction process. For example, signal information in an angiographic study may be known to include structures such as blood vessels. That being the case, when a backprojection path passes through these structures a more accurate distribution of a signal sample in each pixel can be achieved by weighting the distribution as a function of the known signal information at that pixel location. In HYPR, for a backprojection path having N pixels the highly constrained backprojection may be expressed as follows:

$$S_n = \frac{(P \times C_n)}{\sum_{n=1}^{N} C_n},$$

where: $S_n$ is the backprojected signal magnitude at a pixel n in an image frame being reconstructed, P is the signal sample value in the projection profile being backprojected, and $C_n$ is the signal value of an a priori composite image at the $n^{th}$ pixel along the backprojection path. The composite image is reconstructed from data acquired during the scan, and may include that used to reconstruct the given image frame as well as other acquired image data that depicts the structures in the field of view. The numerator in the equation above, $(P \times C_n)$, weights each pixel using the corresponding signal value in the composite image and the denominator, $$\sum_{n=1}^{N} C_n,$$

normalizes the value so that all backprojected signal samples reflect the projection sums for the image frame and are not multiplied by the sum of the composite image.

Further, a new mathematical framework for image reconstruction termed "compressed sensing" (CS) is an emerging technique in which only a small set of linear projections of a sparse image are required to reconstruct a quality image. The theory of CS is described in E. Candès, J. Romberg, and T. Tao, "Robust uncertainty principles: Exact signal reconstruction from highly incomplete frequency information," *IEEE Transactions on Information Theory* 2006; 52:489-509, and D. Donoho, "Compressed sensing," *IEEE Transactions on Information Theory* 2006; 52:1289-1306. The principles of CS are applicable to medical imaging and can therefore be extended to provide a general framework stating that quality medical images can be reconstructed from substantially fewer measurements than through conventional methods.

SUMMARY OF THE INVENTION

The present invention provides an image reconstruction method applicable to a number of different imaging modalities including magnetic resonance imaging (MRI), x-ray computed tomography (CT), positron emission tomography (PET), and single photon emission computed tomography (SPECT). In this method, a sparsifying image is reconstructed from acquired data to provide a priori knowledge of the subject being imaged. An iterative reconstruction process is employed to iteratively determine a correction image for a given image frame that when subtracted from the sparsifying image produces a quality image for the image frame.

A general object of the invention is to improve the reconstruction of medical images by constraining the reconstruction process with a priori information regarding the subject of the image. A sparsifying image is reconstructed from a series of acquired undersampled image data sets and is employed to produce quality images from the undersampled data sets. Correction images are produced for each image data set from which a quality image is sought to be produced. Each of said images is subsequently produced by subtracting the corresponding correction image from the sparsifying image. The improvement resulting from the present invention can manifest itself in a number of ways, including reduction of scan time, reduction in radiation dose, and higher temporal resolution in time-resolved studies.

Another object of the invention is to improve the quality of previously reconstructed images in a series of images having poor quality. A plurality of image data sets are produced by reprojecting the corresponding images into Radon space, and a sparsifying image is produced therefrom. An iterative reconstruction process is employed to produce a correction image corresponding to one of the image data sets. This correction image is subsequently subtracted from the sparsifying image to produce a higher quality version of the corresponding original image. This process is repeated for each image in the series of original, lower quality, images.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

GENERAL DESCRIPTION OF THE INVENTION

Figure 1:
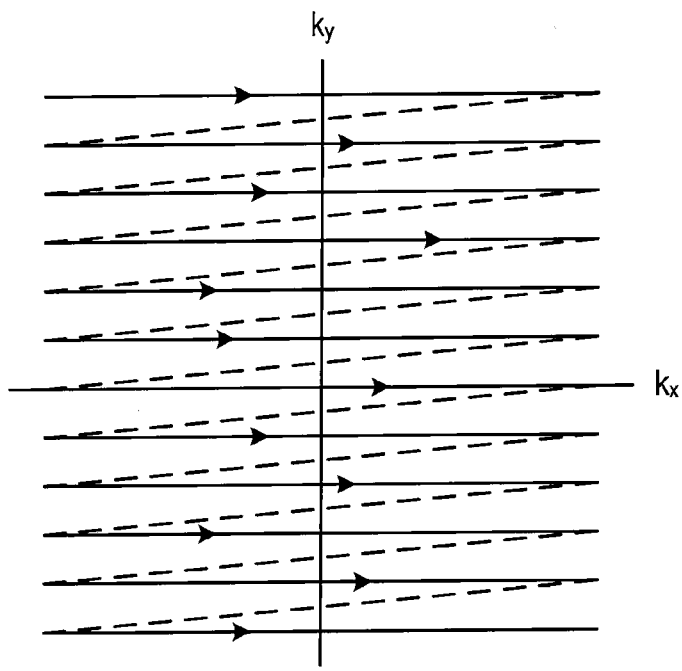
FIG. 1 is a graphic illustration of the manner in which k-space is sampled during a typical Fourier, or spin-warp, image acquisition using an MRI system.

To estimate the underlying image f from an incomplete dataset along compressed sensing guidelines, the following problem is solved:

$$\min_f \{\|Ef - s\|_2^2 + \lambda\|\Psi f\|_1\}, \qquad (1)$$

Where E is the encoding matrix, s is a vector containing the image data acquired with the imaging system, λ is a control parameter that balances the residual error of the minimization process and the sparsity of the image f, and Ψ is a sparsifying matrix. The sparsifying matrix, Ψ, can be any number of matrices that operate to sparsify an object. In the alternative, Ψ can be the identity matrix. For image data that is acquired with radial sampling projections (e.g., radial MRI, computed tomography, positron emission tomography) the encoding matrix E is the Radon transform matrix and s is a vector containing sinogram space values. In the alternative, if the image data is k-space data that is either initially acquired in a Cartesian sampling pattern or non-Cartesian k-space samples regridded to a Cartesian grid, E is the Fourier transform matrix and s is a vector containing k-space values. The image, f, is the underlying image sought to be reconstructed.

Often, data are sampled in a temporal or parametric dimension and possess a significant degree of redundancy, as image pixels may highly correlate along such a dimension. For example, the background tissues in a time-resolved angiographic imaging study will contain substantially the same pixel information. Likewise, in diffusion studies, gray matter exhibits substantially isotropic diffusion behavior and thus, gray matter pixels for different diffusion gradient directions will be highly correlated. This property can be exploited in the compressed sensing framework through the following:

$$\min_f \{\|Ef - s\|_p + \lambda\|\Psi(f - f_s)\|_1\}, \qquad (2)$$

Where $f_s$ is a sparsifying image which is a reasonable estimate of image intensity distribution and $\|\ldots\|_p$ is the p-norm, which for an arbitrary vector x with length K has the form:

$$\|X\|_p = \left(\sum_{k=1}^{K} |x_k|^p\right)^{\frac{1}{p}},$$

And where $0 \leq p \leq \infty$.

The sparsifying image, $f_s$, may be produced by a number of different methods including but not limited to a sliding window reconstruction. In the alternative, the sparsifying image can be reconstructed using other image reconstruction methods such as, for example, HYPR, which is described in co-pending U.S. patent application Ser. No. 11/482,372; HYPR-LR, which is described in co-pending U.S. patent application Ser. No. 12/032,240; and I-HYPR, which is described in co-pending U.S. patent application Ser. No. 12/032,262. By employing the HYPR-LR method, for example, a further increase in the signal-to-noise ratio (SNR) is possible in the desired image frame.

As an example, consider a series of undersampled data sets acquired with a medical imaging system over a period of time, such that a dynamic process is imaged. An exemplary situation could be a series of image data sets acquired during the passage of a contrast agent through the vasculature of a patient. Each individual image data set can be reconstructed to produce an image frame; however, these image frames will be of poor quality as a result of undersampling artifacts. In this situation, a sparsifying image, $f_s$, can be reconstructed from a plurality of the image data sets to produce a reasonable representation of the image intensity throughout the series of image frames. In order to reconstruct a quality image frame, equation (2) above can be employed in an iterative reconstruction method to produce a correction image indicative of the information present in the sparsifying image that does not form a part of the desired underlying image frame. In this manner, equation (2) is rewritten as:

$$\min_{f_{corr}} \{\|s_{corr} - Ef_{corr}\|_p + \lambda\|\Psi f_{corr}\|_1\}, \qquad (3)$$

Where:

$s_{corr} = Ef_s - s$ is a vector containing corrected image data; and $f_{corr} = f_s - f$ is the correction image. Therefore, by iteratively minimizing equation (3), a correction image, $f_{corr}$, is produced that when subtracted from the sparsifying image, $f_s$, results in a quality estimate of the desired underlying image frame, f. Other minimization problems similar to the one described in equation (3) can further be employed to practice the present invention. These include:

$$\min_{f_{corr}} \{\|s_{corr} - Ef_{corr}\|_2^2 + \lambda \|\Psi f_{corr}\|_q^q\}, \quad (4)$$

Where $1 \leq q \leq 2$, and $(\ldots)^q$ indicates the conventional $q^{th}$ power operation.

DETAILED DESCRIPTION OF THE PREFERRED EMBODIMENT

The present invention may be applied to many different medical imaging modalities and to many different clinical applications. A number of these clinical applications of the invention are described below to illustrate the broad scope of the present invention. While the preferred embodiment of the present invention is to reconstruct an image from data acquired with a medical imaging system, it should be appreciated to those skilled in the art that it is possible to use the present invention to improve the quality of existing images. Such existing images may be decomposed into a set of projection views and a new image can be reconstructed from them using the reconstruction method of the present invention. The improvement will depend, of course, on the quality of the sparsifying image that is used, and this in turn will depend on the available a priori information regarding the subject being imaged.

Magnetic Resonance Imaging System

Figure 3:
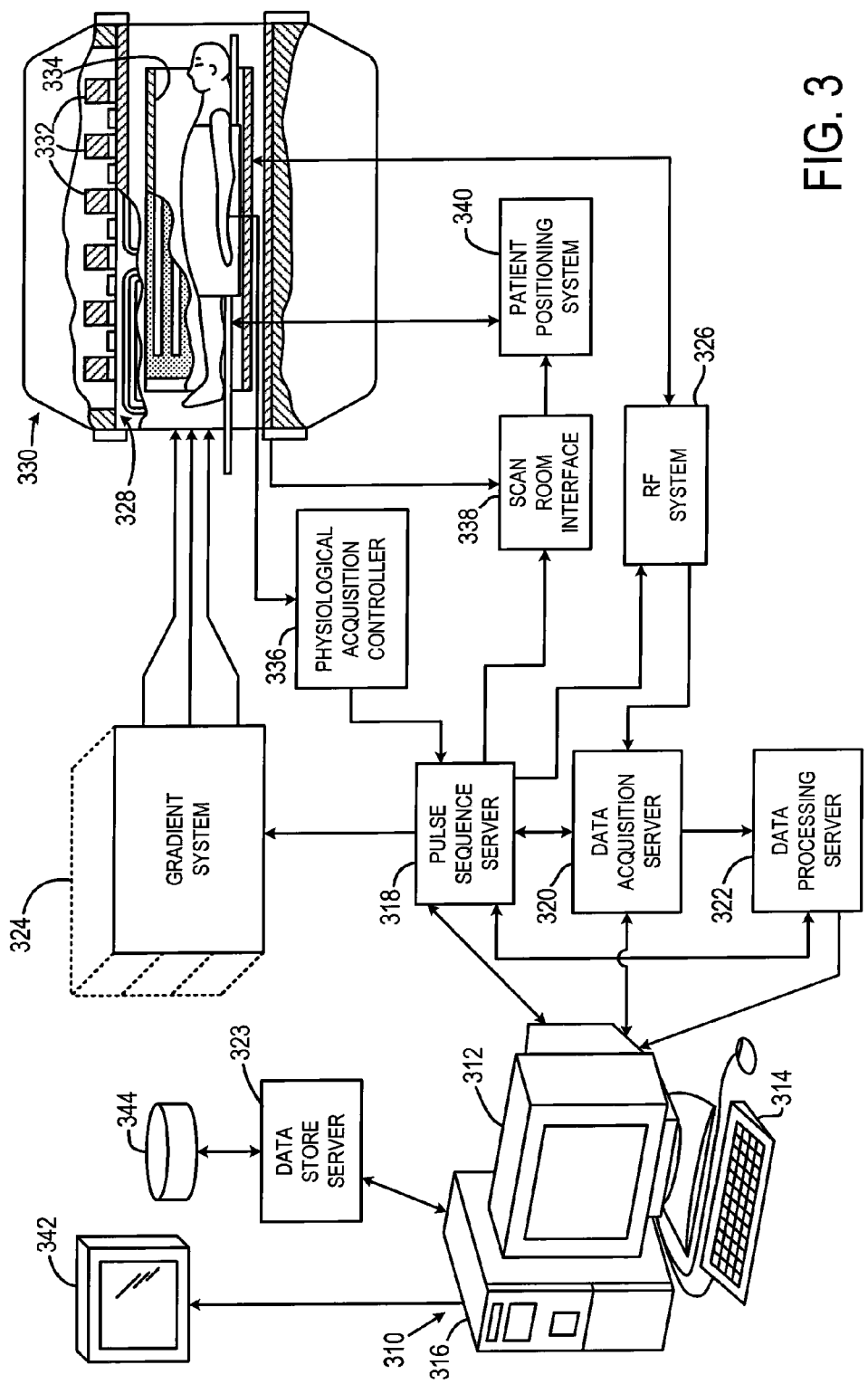
FIG. 3 is a block diagram of a magnetic resonance imaging (MRI) system used to practice the present invention.

Referring particularly to FIG. 3, one embodiment of the invention is employed in an MRI system. The MRI system includes a workstation 310 having a display 312 and a keyboard 314. The workstation 310 includes a processor 316 that is a commercially available programmable machine running a commercially available operating system. The workstation 310 provides the operator interface that enables scan prescriptions to be entered into the MRI system. The workstation 310 is coupled to four servers: a pulse sequence server 318; a data acquisition server 320; a data processing server 322, and a data store server 323. The workstation 310 and each server 318, 320, 322 and 323 are connected to communicate with each other.

The pulse sequence server 318 functions in response to instructions downloaded from the workstation 310 to operate a gradient system 324 and an RF system 326. Gradient waveforms necessary to perform the prescribed scan are produced and applied to the gradient system 324 that excites gradient coils in an assembly 328 to produce the magnetic field gradients $G_x$, $G_y$, and $G_z$ used for position encoding MR signals. The gradient coil assembly 328 forms part of a magnet assembly 330 that includes a polarizing magnet 332 and a whole-body RF coil 334.

RF excitation waveforms are applied to the RF coil 334 by the RF system 326 to perform the prescribed magnetic resonance pulse sequence. Responsive MR signals detected by the RF coil 334 or a separate local coil (not shown in FIG. 3) are received by the RF system 326, amplified, demodulated, filtered and digitized under direction of commands produced by the pulse sequence server 318. The RF system 326 includes an RF transmitter for producing a wide variety of RF pulses used in MR pulse sequences. The RF transmitter is responsive to the scan prescription and direction from the pulse sequence server 318 to produce RF pulses of the desired frequency, phase and pulse amplitude waveform. The generated RF pulses may be applied to the whole body RF coil 334 or to one or more local coils or coil arrays (not shown in FIG. 3).

The RF system 326 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2},$$

and the phase of the received MR signal may also be determined:

$$\phi = \tan^{-1}\left(\frac{Q}{I}\right).$$

The pulse sequence server 318 also optionally receives patient data from a physiological acquisition controller 336. The controller 336 receives signals from a number of different sensors connected to the patient, such as ECG signals from electrodes or respiratory signals from a bellows. Such signals are typically used by the pulse sequence server 318 to synchronize, or "gate", the performance of the scan with the subject's respiration or heart beat.

The pulse sequence server 318 also connects to a scan room interface circuit 338 that receives signals from various sensors associated with the condition of the patient and the magnet system. It is also through the scan room interface circuit 338 that a patient positioning system 340 receives commands to move the patient to desired positions during the scan.

The digitized MR signal samples produced by the RF system 326 are received by the data acquisition server 320. The data acquisition server 320 operates in response to instructions downloaded from the workstation 310 to receive the real-time MR data and provide buffer storage such that no data is lost by data overrun. In some scans the data acquisition server 320 does little more than pass the acquired MR data to the data processor server 322. However, in scans that require information derived from acquired MR data to control the further performance of the scan, the data acquisition server 320 is programmed to produce such information and convey it to the pulse sequence server 318. For example, during prescans MR data is acquired and used to calibrate the pulse sequence performed by the pulse sequence server 318. Also, navigator signals may be acquired during a scan and used to adjust RF or gradient system operating parameters or to control the view order in which k-space is sampled. And, the data acquisition server 320 may be employed to process MR signals used to detect the arrival of contrast agent in an MRA scan. In all these examples the data acquisition server 320 acquires MR data and processes it in real-time to produce information that is used to control the scan.

The data processing server 322 receives MR data from the data acquisition server 320 and processes it in accordance with instructions downloaded from the workstation 310. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 322 are conveyed back to the workstation 310 where they are stored. Real-time images are stored in a data base memory cache (not shown) from which they may be output to operator display 312 or a display that is located near the magnet assembly 330 for use by attending physicians. Batch mode images or selected real time images are stored in a host database on disc storage 344. When such images have been reconstructed and transferred to storage, the data processing server 322 notifies the data store server 323 on the workstation 310. The workstation 310 may be used by an operator to archive the images, produce films, or send the images via a network to other facilities.

Preferred Pulse Sequence

Figure 4:
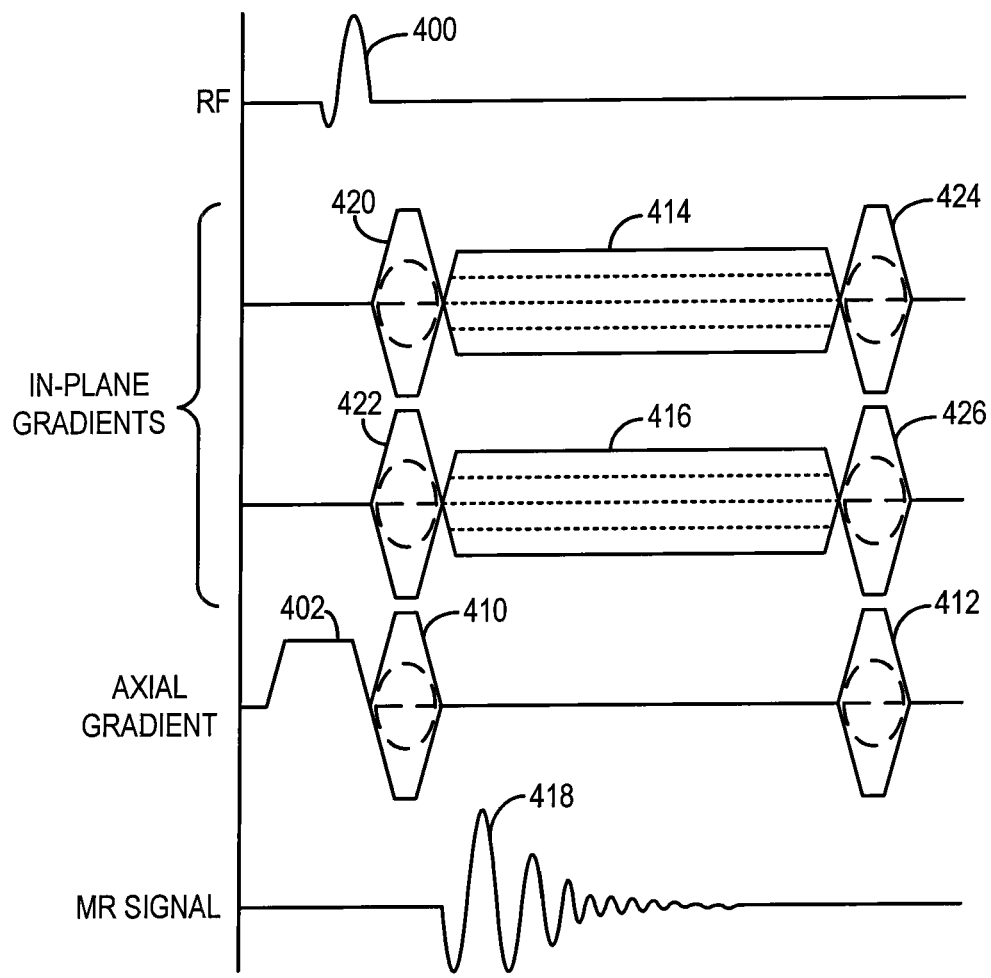
FIG. 4 is a pulse sequence used in the MRI system of FIG. 3 to practice one embodiment of the invention.
Figure 5:
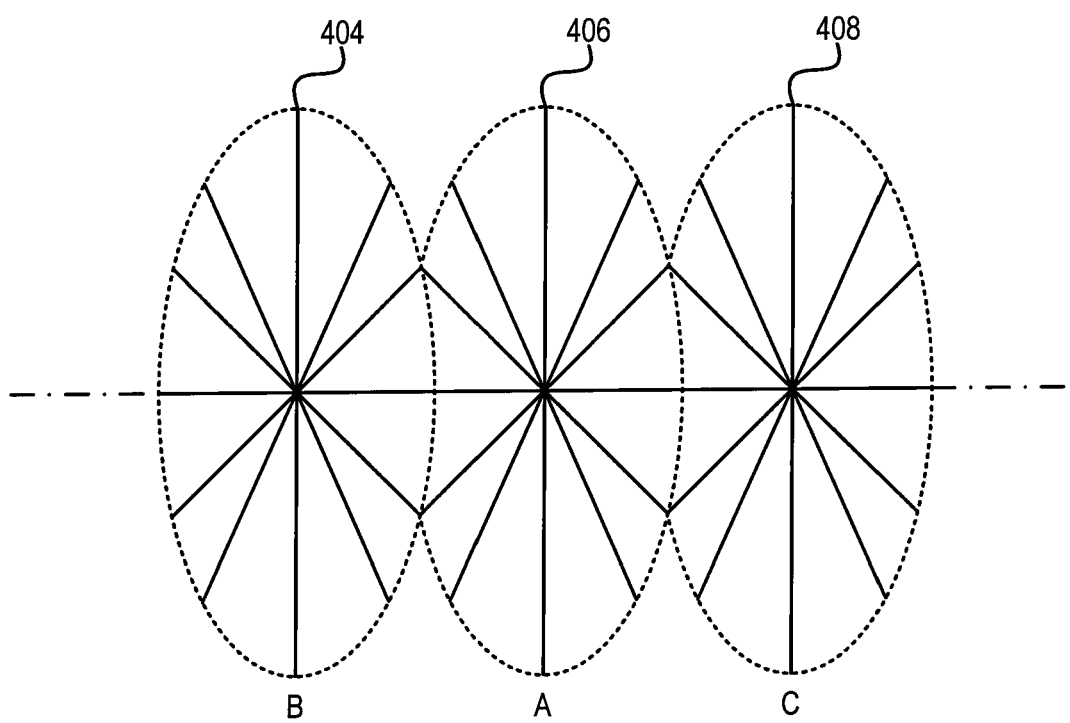
FIG. 5 is a pictorial representation of the k-space data sampled using the pulse sequence of FIG. 4.

To practice the preferred embodiment of the invention NMR data is acquired using a projection reconstruction, or radial, pulse sequence shown in FIG. 4. This is a fast gradient-recalled echo pulse sequence in which a selective, asymmetrically truncated sinc RF excitation pulse 400 is produced in the presence of a slice-select gradient 402. This pulse sequence may be used to acquire a single 2D slice by sampling in a single k-space circular plane, or it may be used to sample a plurality of circular k-space planes as shown at 404, 406 and 408 in FIG. 5. When multiple 2D slices are acquired the gradient 402 is a slab select gradient followed by a phase encoding gradient lobe 410 and a rewinder gradient lobe 412 of opposite polarity. This axial, phase encoding gradient 410 is stepped through values during the scan to sample from each of the 2D k-space planes 404, 406 and 408.

Two in-plane readout gradients 414 and 416 are played out during the acquisition of an NMR echo signal 418 to sample k-space in a 2D plane 404, 406 or 408 along a radial trajectory. These in-plane gradients 414 and 416 are perpendicular to the axial gradient and they are perpendicular to each other. During a scan they are stepped through a series of values to rotate the view angle of the radial sampling trajectory as will be described in more detail below. Each of the in-plane readout gradients is preceded by a prephasing gradient lobe 420 and 422 and followed by a rewinder gradient lobe 424 and 426.

It should be apparent to those skilled in the art that sampling trajectories other than the preferred straight line trajectory extending from one point on the k-space peripheral boundary, through the center of k-space to an opposite point on the k-space peripheral boundary may also be used. One variation is to acquire a partial NMR echo signal 418 which samples along a trajectory that does not extend across the entire extent of the sampled k-space volume. An exemplary pulse sequence for this method can be found, for example, in U.S. Pat. No. 7,148,685. Another variation which is equivalent to the straight line projection reconstruction pulse sequence is to sample along a curved path, or spiral, rather than a straight line. Such pulse sequences are described, for example, in "Fast Three Dimensional Sodium Imaging", MRM, 37:706-715, 1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia. It should further be appreciated by those skilled in the art that Cartesian sampling patterns can also be interleaved and employed to practice the present invention. Moreover, the present invention may be employed with 3D as well as 2D versions of these sampling methods and use of the term "pixel" herein is intended to refer to a location in either a 2D or a 3D image.

The MRI system described above can be used in a wide variety of clinical applications to acquire either 2D or 3D sets of projection views that may be used to reconstruct one or more images. The image reconstruction method of the present invention is particularly useful in scans where one or more image frames are reconstructed using less than all the acquired projection views. The present invention can further be practiced with parallel MR imaging techniques, as will be described in better detail below.

Image Reconstruction for MR Imaging System

Figure 2:
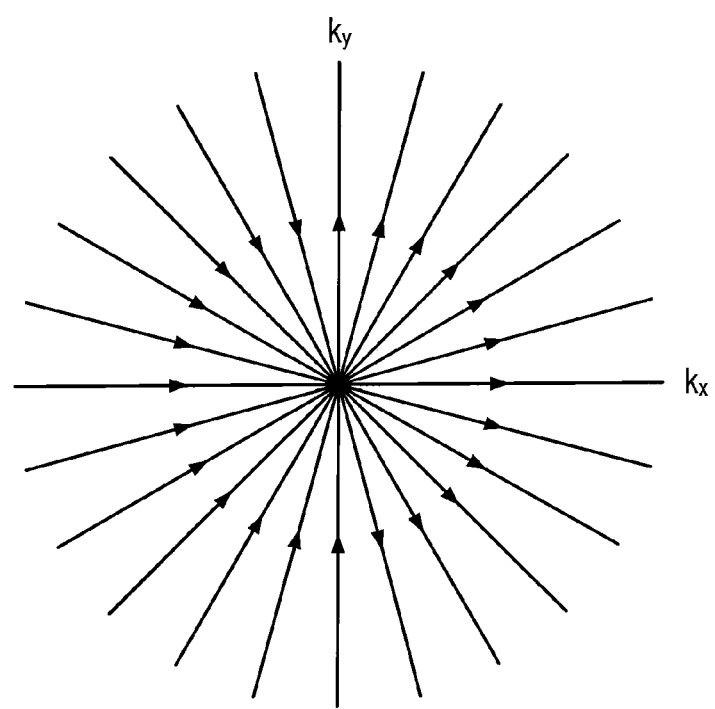
FIG. 2 is a graphic illustration of the manner in which k-space is sampled during a typical projection reconstruction image acquisition using an MRI system.
Figure 6:
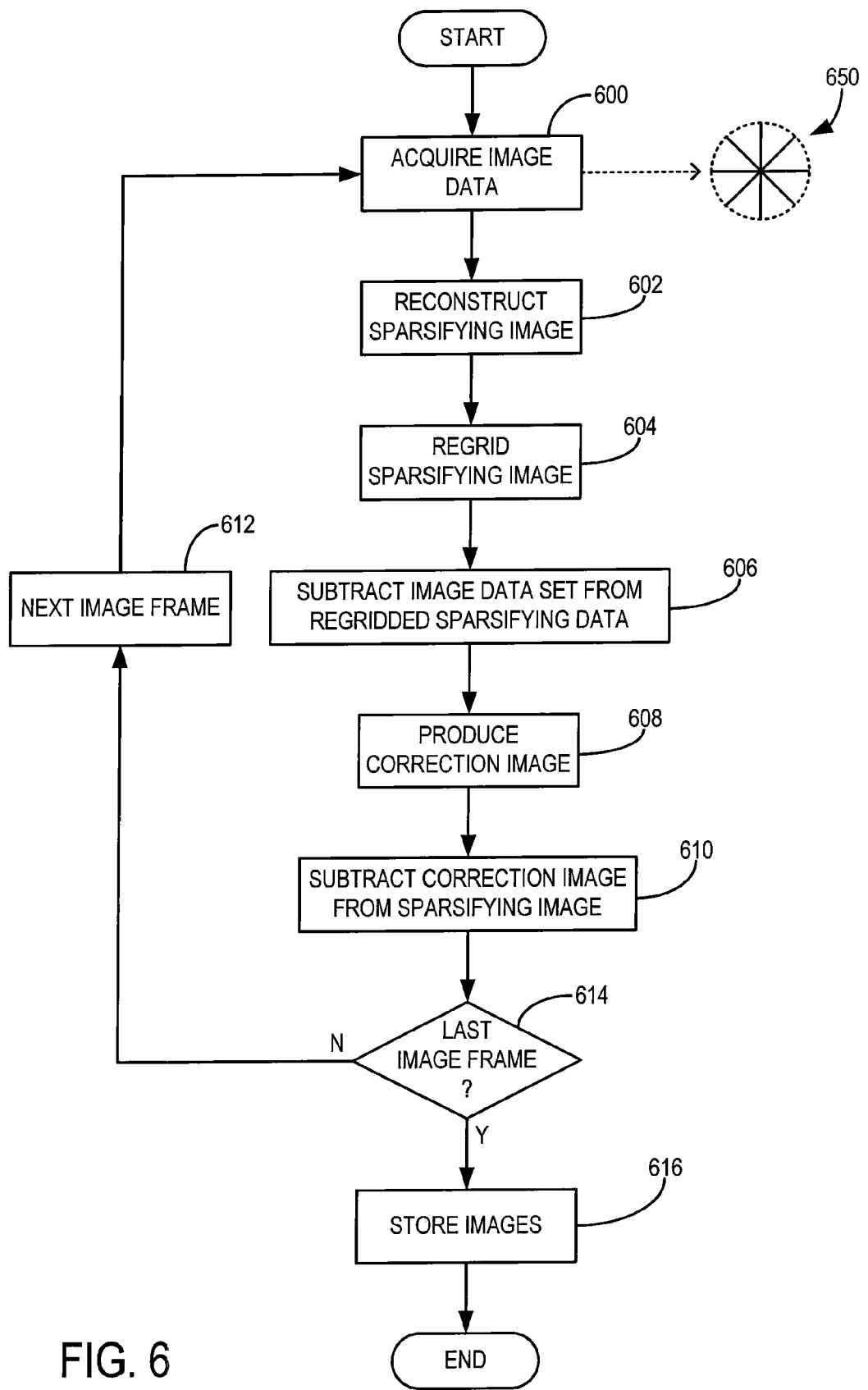
FIG. 6 is a flowchart of an embodiment of the invention used in the MRI system of FIG. 3 with the pulse sequence of FIG. 4.

The first embodiment of the image reconstruction method employs an MRI system that acquires two-dimensional projection views and reconstructs a series of image frames that depict the subject over a period of time. Referring particularly to FIG. 6, a set of projection views 650 are acquired from which an image frame is to be reconstructed as indicated at process block 600. These projection views 650 are few in number (e.g., 10 views) and evenly distributed to sample k-space as uniformly as possible as illustrated in FIG. 2. Because of the low number of projection views that are acquired, this image frame can be acquired in a very short scan time, but because k-space is highly undersampled, streak artifacts will occur in any image reconstructed using conventional methods. The use of the term image data set herein is intended to refer to a set of projection views 650 acquired with a preselected number of repetitions of the pulse sequence described above with reference to FIG. 4.

Figure 7:
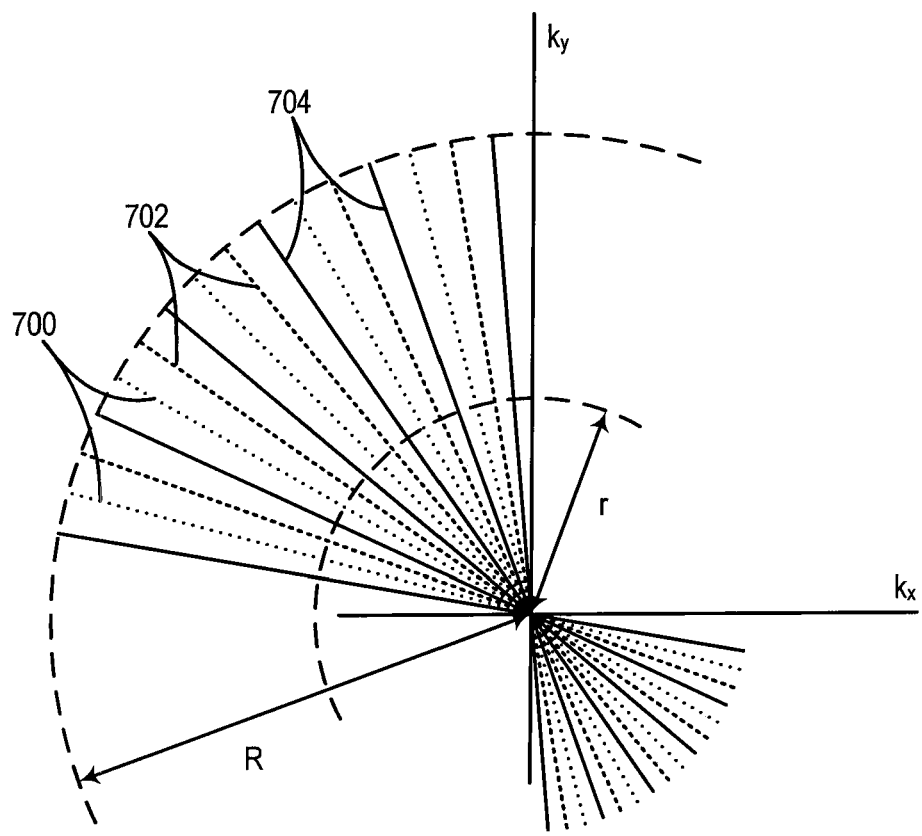
FIG. 7 is a graphic representation of interleaved projection views.

The next step as indicated at process block 602 is to combine all of the projection views that have been acquired from the subject of the examination and reconstruct a composite, or sparsifying, image, $f_s$. This will include projection views previously acquired which are interleaved with the views for the current image frame and which thus provides a more complete sampling of k-space. Referring to FIG. 7, for example, the current image frame projection views may sample k-space as indicated by dotted lines 700 and previously acquired image frame views may sample k-space as indicated by dashed lines 702 and lines 704. The sparsifying image may be reconstructed using a conventional method because a sufficient number of views are available to avoid image artifacts. In the preferred embodiment this reconstruction includes regridding the combined acquired k-space projection data into Cartesian coordinates and then performing an inverse two-dimensional Fourier transformation (2DFT) to produce the sparsifying image, $f_s$.

The current image frame is next reconstructed according to the teachings of the present invention. More specifically, the sparsifying image, $f_s$, is regridded into k-space along the same sampling pattern as the current image frame, as indicated in step 604. An exemplary regridding process is described in K P Pruessman, et al., "Advances in Sensitivity Encoding With Arbitrary k-Space Trajectories" Magn. Reson. Med. 2001; 46:638-651. The current image data set is then subtracted from the regridded sparsifying image in step 606 to produce a difference data set. Since the sparsifying image has been regridded in the manner described above, it is no longer an interleaved set of k-space projection views as shown in FIG. 7; instead, the regridded data is a set of values in k-space having the same sampling pattern as the current image data set, but including information corresponding to a plurality of image frames. Therefore, when the subtraction occurs, the information contained in the current image data set is not simply removed from the regridded data as would be the case were the current image data set to be subtracted from the sliding window composite of the image frames acquired in step 600.

A correction image is produced next in step 608. First, the k-space projection views in the difference data set are transformed to Radon, or sinogram, space by performing a one-dimensional, fast Fourier inverse transformation to produce the vector $s_{corr}$. This is repeated for each projection view in the difference data set to form a matrix of difference data vectors, $s_{corr}$. The encoding matrix, E, is then selected to be a Radon transform matrix. In the alternative, the matrix of difference data vectors, $s_{corr}$, can contain k-space values and the corresponding encoding matrix, E, can be selected as a Fourier transform matrix. A fixed value of the control parameter, $\lambda$, and an appropriate sparsifying transform $\Psi$ are selected and the minimization problem presented in equation (3) is iteratively solved to produce the correction image for the current image frame. The minimization problem is solved using an iteratively reweighed algorithm such as the one described in I F Gorodnitsky and B D Rao, "Sparse Signal Reconstruction from Limited Data Using FOCUSS: A Re-weighted Minimum Norm Algorithm" *IEEE Transactions on Signal Processing,* 1997; 45(3):600-616. In the alternative, other iterative algorithms may be employed, such as, for example, the one described in B Wohlberg and P Rodriguez, "An Iteratively Reweighted Norm Algorithm for Minimization of Total Variation Functionals" *IEEE Signal Processing Letters,* 2007; 14(12):948-951. In the preferred embodiment, the sparsifying transform, $\Psi$, is selected to be an image gradient D, where D is a matrix of first order image differences. In the alternative, however, $\Psi$ can be selected to be a discrete wavelet transform or an identity matrix. The choice of $\Psi$ can vary and it should be appreciated by those skilled in the art that many variations are possible and are all within the scope of the present invention.

The correction image, $f_{corr}$, has pixel values indicative of image intensity differences between the sparsifying image and the underlying current image frame. As such, the final image corresponding to the current image frame is then produced in step 610 where the correction image is subtracted from the sparsifying image, $f_s$. The a priori information embodied in the sparsifying image is used to constrain and thereby improve the quality of the reconstructed image frames.

Additional image frames are reconstructed as indicated at process block 612. When the last image frame is completed as determined at decision block 614, the reconstruction process stops and all the image frames are stored as indicated at process block 616.

Parallel Image Reconstruction for MR Imaging System

Figure 8:
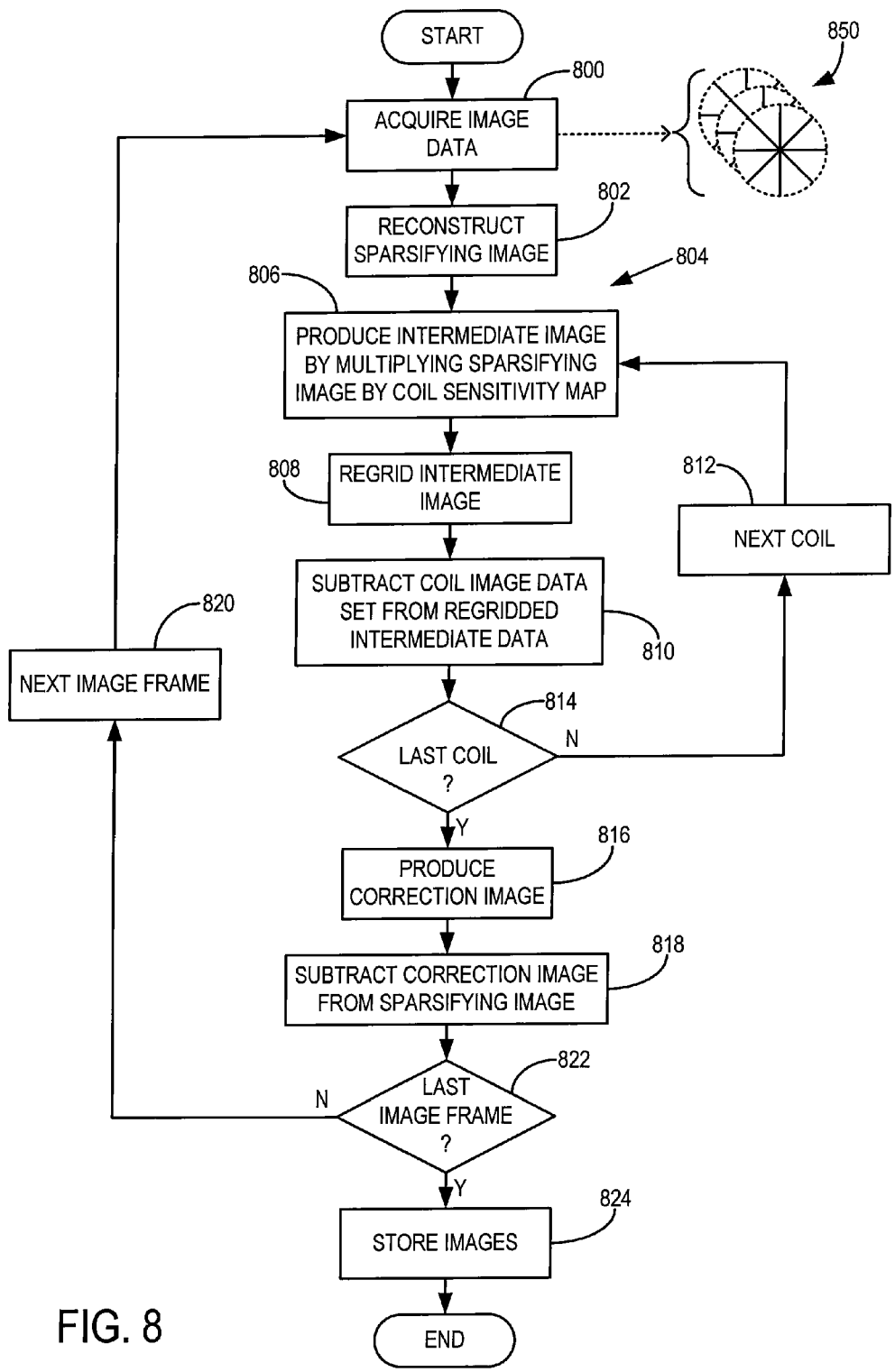
FIG. 8 is a flowchart of another embodiment of the invention used in the MRI system of FIG. 3 with the pulse sequence of FIG. 4.

Another embodiment of the image reconstruction method also employs an MRI system that acquires two-dimensional projection views and reconstructs a series of image frames that depict the subject over a period of time. In this embodiment, however, the image data is acquired using a parallel RF receive coil array and one image data set is acquired from each receive coil element, collectively forming a "coil image data set" 850. Referring particularly to FIG. 8, a coil image data set is acquired from which an image frame is to be reconstructed as indicated at process block 800. The projection views making up each image data set within the coil image data set 850 are few in number and evenly distributed to sample k-space as uniformly as possible as illustrated in FIG. 2. Because of the low number of projection views that are acquired, each image frame can be acquired in a very short scan time, but because k-space is highly undersampled, streak artifacts will occur in any image reconstructed using conventional methods. By employing a parallel MR acquisition scheme, an even further reduction of overall scan time is achievable.

The next step as indicated at process block 802 is to combine all of the projection views that have been acquired from the subject of the examination and reconstruct a composite, or sparsifying, image, $f_s$. First, the image data sets for each coil element in the parallel receiver array are combined. Each of these combined image data sets will include projection views previously acquired which are interleaved with the views for the current image frame and which thus provides a more complete sampling of k-space. Referring to FIG. 7, for example, the current image frame projection views may sample k-space as indicated by dotted lines 700 and previously acquired image frame views may sample k-space as indicated by dashed lines 702 and lines 704. However, k-space is still undersampled and parallel MR image reconstruction methods are employed to produce a sparsifying image, $f_s$, from the combined image data sets from each coil element. The sparsifying image may be reconstructed using a conventional parallel reconstruction method with the choice of reconstruction method depending on the k-space trajectory employed to practice the present invention. For example, a non-Cartesian SENSE method can be employed, such as the one described in K P Pruessman, et al., "Advances in Sensitivity Encoding With Arbitrary k-Space Trajectories" *Magn. Reson. Med.* 2001; 46:638-651.

A loop is then entered at 804, in which a sparsified image data set is produced from the coil image data set 850. More specifically, for each coil element the sparsifying image, $f_s$, is first multiplied by the corresponding coil sensitivity map, as indicated in step 806 to produce an intermediate image. Each intermediate image is then regridded into k-space along the same sampling pattern as the current image frame in step 808. An exemplary regridding process is described in K P Pruessman, et al., "Advances in Sensitivity Encoding With Arbitrary k-Space Trajectories" *Magn. Reson. Med.* 2001; 46:638-651. The current image data set for the corresponding coil element is then subtracted from the regridded intermediate image in step 810 to produce a difference data set for that coil. This process is repeated for the image data set corresponding to the next coil element, as indicated in step 812. When a difference data set has been produced for the current image frame for each coil in the parallel receiver array, as determined at decision block 814, the reconstruction process for the current image frame continues.

A correction image is produced next in step 816. First, the k-space projection views in the difference data set are transformed to Radon, or sinogram, space by performing a one-dimensional, fast Fourier inverse transformation to produce the vector $s_{corr}$, and an appropriate encoding matrix, E, is further produced. Additionally, each difference data vector, $s_{corr}$, includes information for a given projection view from each coil in the parallel receiver coil array. As described above, the difference data vectors, $s_{corr}$, can alternatively contain k-space values. A fixed value of the control parameter, $\lambda$, and an appropriate sparsifying transform $\Psi$ are selected and the minimization problem presented in equation (3) is iteratively solved to produce the correction image for the current image frame. In this embodiment, the encoding matrix E is selected to include the coil sensitivity profiles of each coil element in the parallel receiver array. The minimization problem is then solved using an iteratively reweighed algorithm such as the one described in I F Gorodnitsky and B D Rao, "Sparse Signal Reconstruction from Limited Data Using FOCUSS: A Re-weighted Minimum Norm Algorithm" *IEEE Transactions on Signal Processing* 1997; 45(3): 600-616. In the preferred embodiment, the sparsifying transform, $\Psi$, is selected to be an image gradient D, where D is a matrix of first order image differences. In the alternative, $\Psi$ can be selected to be a discrete wavelet transform or an identity matrix. The choice of $\Psi$ can vary and it should be appreciated by those skilled in the art that many variations are possible and are all within the scope of the present invention.

The final image corresponding to the current image frame is then produced in step 816 where the correction image is subtracted from the sparsifying image, $f_s$. The a priori information embodied in the sparsifying image is used to constrain and thereby improve the quality of the reconstructed image frames. Additional image frames are reconstructed as indicated at process block 820. When the last image frame is completed as determined at decision block 822, the reconstruction process stops and all the image frames are stored as indicated at process block 824.

Computed Tomography Imaging System

Figure 9A:
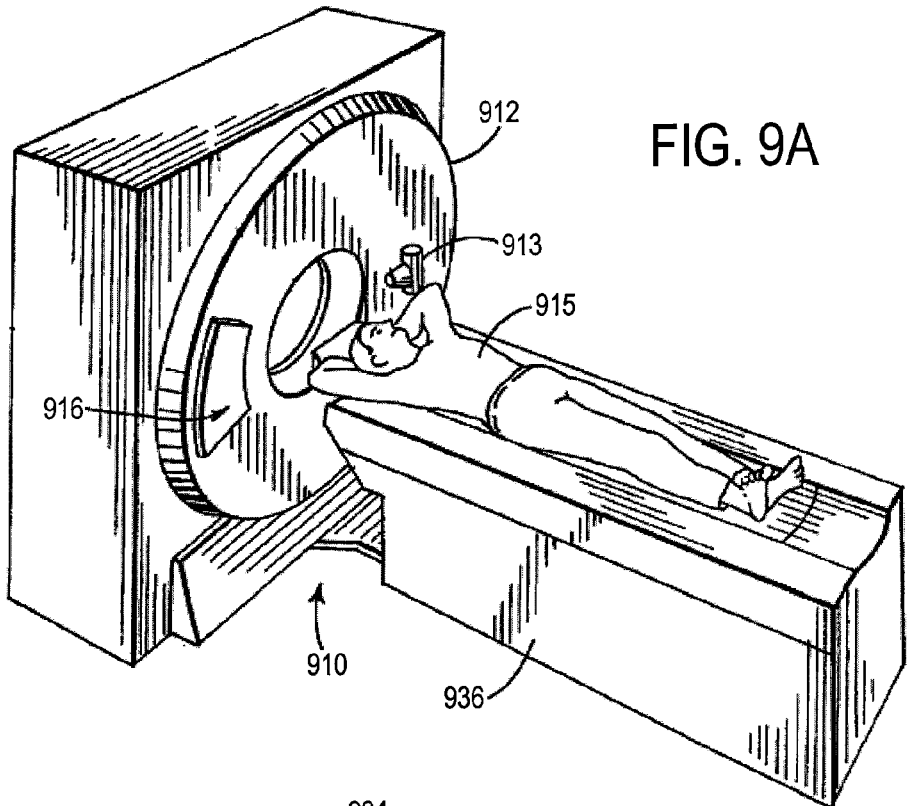
FIG. 9A is a pictorial view of a CT scanner system.
Figure 9B:
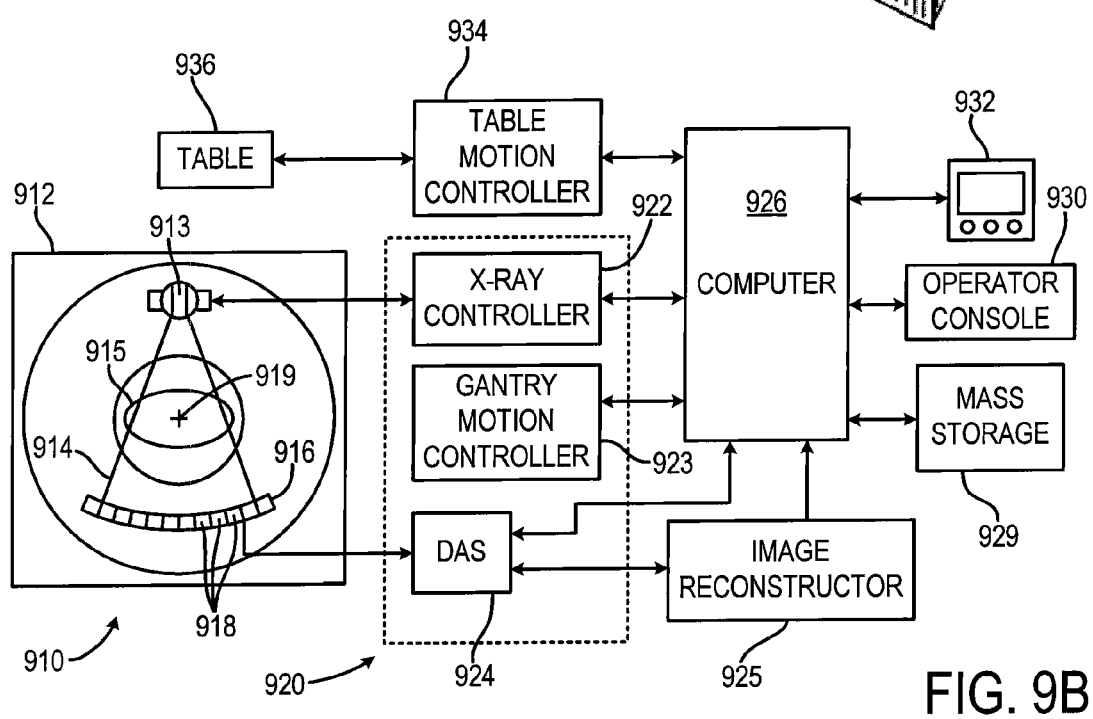
FIG. 9B is a block diagram of the CT scanner system of FIG. 9A.

The present invention is also particularly applicable to other medical imaging modalities in which interleaved projection views of the subject are acquired. One such imaging modality is x-ray computed tomography. With initial reference to FIGS. 9A and 9B, a computed tomography (CT) imaging system 910 includes a gantry 912 representative of a "third generation" CT scanner. Gantry 912 has an x-ray source 913 that projects a fan beam, or cone beam, of x-rays 914 toward a detector array 916 on the opposite side of the gantry. The detector array 916 is formed by a number of detector elements 918 which together sense the projected x-rays that pass through a medical patient 915. Each detector element 918 produces an electrical signal that represents the intensity of an impinging x-ray beam and hence the attenuation of the beam as it passes through the patient. During a scan to acquire x-ray projection data, the gantry 912 and the components mounted thereon rotate about a center of rotation 919 located within the patient 915.

The rotation of the gantry and the operation of the x-ray source 913 are governed by a control mechanism 920 of the CT system. The control mechanism 920 includes an x-ray controller 922 that provides power and timing signals to the x-ray source 913 and a gantry motor controller 923 that controls the rotational speed and position of the gantry 912. A data acquisition system (DAS) 924 in the control mechanism 920 samples analog data from detector elements 918 and converts the data to digital signals for subsequent processing. An image reconstructor 925, receives sampled and digitized x-ray data from the DAS 924 and performs high speed image reconstruction. The reconstructed image is applied as an input to a computer 926 which stores the image in a mass storage device 928.

The computer 926 also receives commands and scanning parameters from an operator via console 930 that has a keyboard. An associated display 932 allows the operator to observe the reconstructed image and other data from the computer 926. The operator supplied commands and parameters are used by the computer 926 to provide control signals and information to the DAS 924, the x-ray controller 922 and the gantry motor controller 923. In addition, computer 926 operates a table motor controller 934 which controls a motorized table 936 to position the patient 915 in the gantry 912.

Like the MRI system, the CT system has many different clinical applications in which either 2D or 3D sets of projection views are acquired and used to reconstruct one or more images of the patient. Whereas the projection views acquired by the MRI system are comprised of k-space (or Fourier space) samples, the projection views acquired by the CT system are comprised of Radon space samples. Image reconstruction using data acquired with a CT system necessarily requires transformation from Radon space to real space.

Image Reconstruction for CT Imaging System

Figure 10:
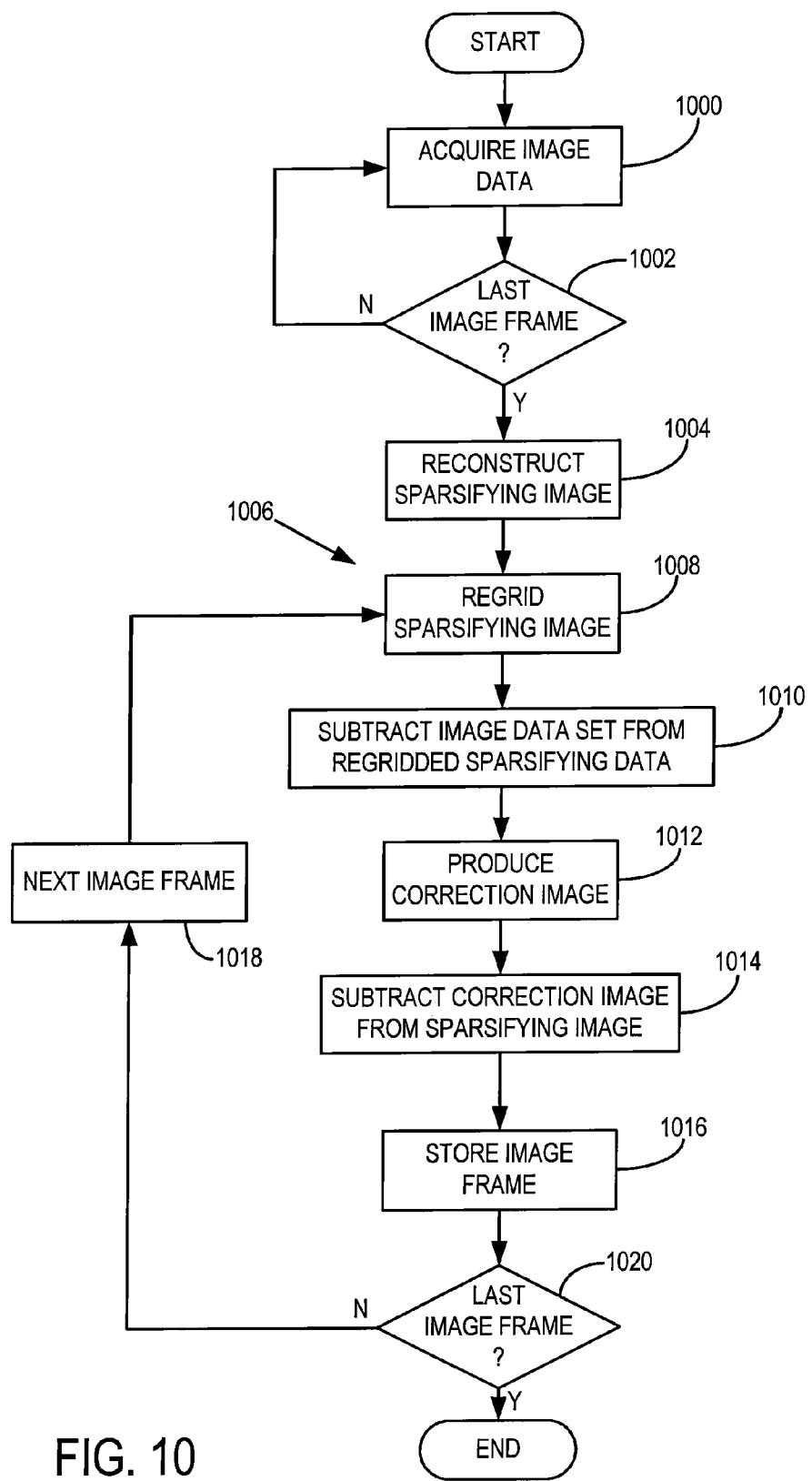
FIG. 10 is a block diagram of another embodiment of the invention using the CT scanner of FIGS. 9A and 9B.

Referring particularly to FIG. 10, another embodiment of the invention employs a CT system to acquire a series of 2D slice images. As indicated by process block 1000 a set of projection views from which a 2D image frame can be reconstructed is acquired. This may be a highly undersampled acquisition in which the projection views are at equally spaced view angles that sample Radon space in a uniform manner as illustrated in FIG. 2. In this embodiment, the data acquisition phase of the scan is completed prior to image reconstruction and a series of image frames are thus acquired before this phase of the scan is completed as determined at decision block 1002. For example, a series of image frames may be acquired during a dynamic study in which a contrast agent flows into the region of interest. As with the first embodiment described above, the projection views acquired during this scan are interleaved as illustrated in FIG. 7 such that when they are all combined, a data set is formed in which Radon space is highly sampled even though each image data set undersamples Radon space.

As indicated at process block 1004, a sparsifying image is reconstructed from the combined projection views acquired during the acquisition phase of the scan. The sets of equally spaced projection views that form each image frame are interleaved with each other such that the projection views from a combination of image frames more fully sample Radon space and produce a higher quality image. The sparsifying image is reconstructed from these combined projection views using a conventional image reconstruction technique such as a filtered backprojection.

A loop is entered into at 1006 where the reconstruction method described above may now be used to reconstruct each frame image. First, the sparsifying image is regridded to the same sampling pattern as the image frame that is to be reconstructed, as indicated in step 1008. Next, the current image data is subtracted from the regridded sparsified data to produce a difference data set in step 1010. The difference data set is then employed in the minimization problem presented in equation (3) above to produce a correction image in step 1012. Since the data acquired with a CT imaging system is inherently in Radon space, the difference data need not be transformed before the iterative minimization process. As described above, the encoding matrix in this situation is the Radon transform matrix and a control parameter $\lambda$, and an appropriate sparsifying transform $\Psi$ are selected. The corrected image frame is then produced in step 1014 by subtracting the correction image from the sparsifying image. The resulting corrected image frame is stored as indicated at process block 1016.

Further image frames are reconstructed as indicated at process block 1018 until all the data acquired during the data acquisition phase of the scan is used as determined at decision block 1020. The reconstruction phase of the scan ends at this point, although the reconstructed image frames may be further processed depending on the particular clinical application. In this embodiment the sparsifying image is formed by all the views acquired during the scan to provide a substantial improvement in image frame SNR, but the image frames are not available in real time.

Positron Emission Tomography Imaging System

In the above-described embodiments the a priori information used to reconstruct the sparsifying image results from the acquisition of a plurality of image frames at interleaved projection views. There are other clinical applications of the present invention, however, in which a priori information is available for a quality sparsifying image without acquiring additional projection views. One of these is data acquired with a positron emission tomography (PET) scanner.

Figure 11:
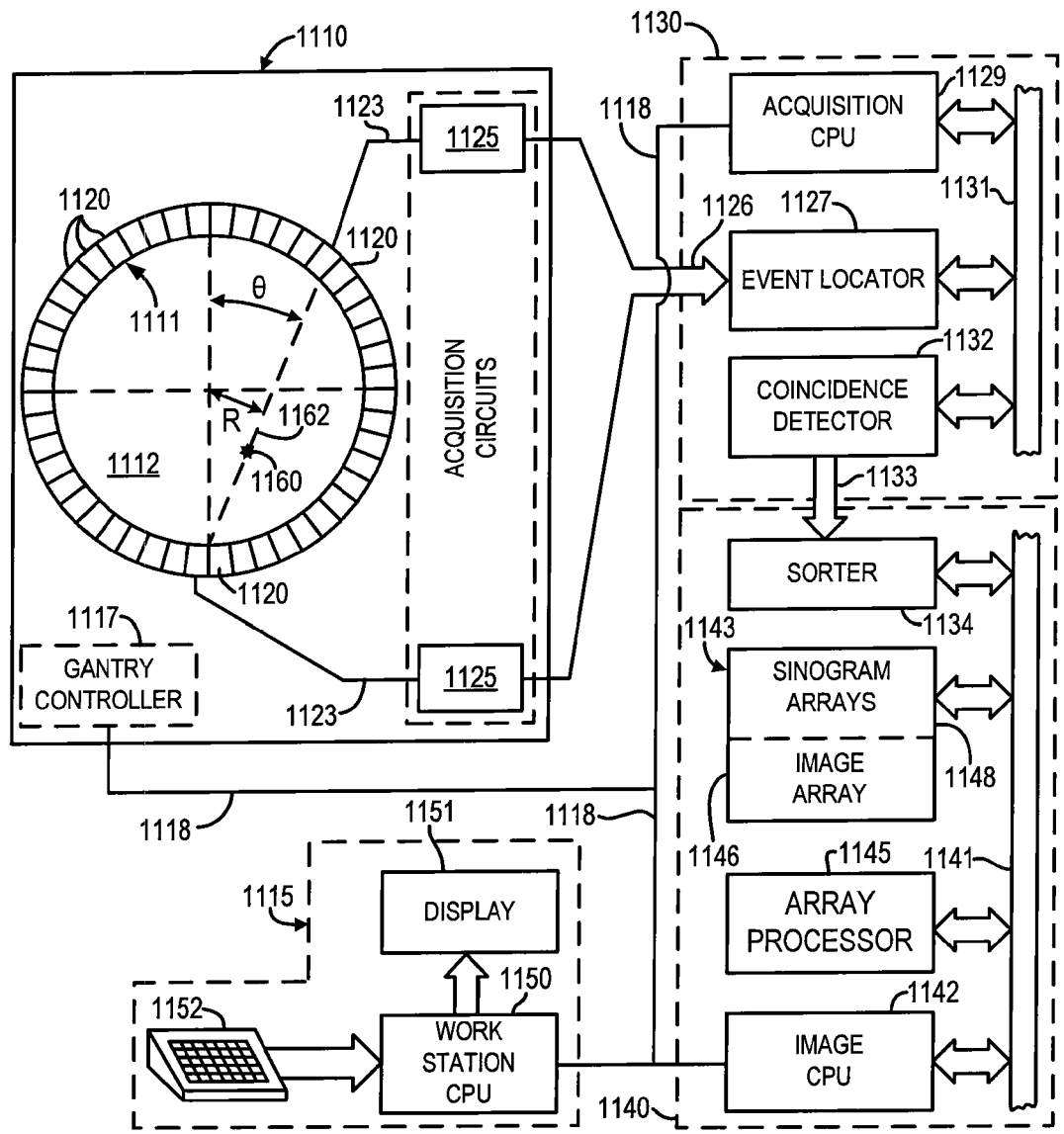
FIG. 11 is a block diagram of a positron emission tomography (PET) scanner.

Referring particularly to FIG. 11, the PET scanner system includes a gantry 1110 which supports a detector ring assembly 1111 about a central opening, or bore 1112. A gantry controller 1117 is mounted within the gantry 1110 and is responsive to commands received from an operator work station 1115 through a second serial communication link 1118 to operate the gantry.

The detector ring 1111 is comprised of detector blocks 1120. Each block 1120 includes a set of scintillator crystal photomultiplier tubes. A set of acquisition circuits 1125 are mounted within the gantry 1110 to receive the signals from each of the modules 1120 in the detector ring 1111. The acquisition circuits 1125 determine the event coordinates within each block of scintillator crystals and these coordinates (x,z), along with the sum of the crystal block signals are digitized and sent through a cable 1126 to an event locator circuit 1127 housed in a separate cabinet 1128. Each acquisition circuit 1125 also produces an event detection pulse (EDP) which indicates the exact moment the scintillation event took place.

The event locator circuits 1127 form part of a data acquisition processor 1130 which periodically samples the signals produced by the acquisition circuits 1125. The processor 1130 has a backplane bus structure 1131 and an acquisition CPU 1129 which controls communications on this bus 1131 and links the processor 1130 to the local area network 1118. The event locator 1127 is comprised of a set of separate circuit boards which each connect to the cable 1126 and receive signals from corresponding acquisition circuits 1125 in the gantry 1110. The event locator 1127 synchronizes the event with the operation of the processor 1130 by detecting the event pulse (EDP) produced by an acquisition circuit 1125, and converting it into an 8-bit time marker which indicates when within the current sample period the scintillation event took place. Also, this circuit 1127 discards any detected events if the total energy of the scintillation is outside the range of 511 keV±20%. During each sample period, the information regarding each valid event is assembled into a set of digital numbers that indicate precisely when the event took place and the position of the scintillator crystal which detected the event. This event data packet is conveyed to a coincidence detector 1132 which is also part of the data acquisition processor 1130.

The coincidence detector 1132 accepts the event data packets from the event locators 1127 and determines if any two of them are in coincidence. Events which cannot be paired are discarded, but coincident event pairs are located and recorded as a coincidence data packet that is conveyed through a serial link 1133 to a sorter 1134. Each coincidence data packet includes a pair of digital numbers which precisely identify the addresses of the two scintillator crystals that detected the event. From these, the location and angle of the ray path that produced the coincidence event can be determined.

The sorter 1134 is a circuit which forms part of an image reconstruction processor 1140. The image reconstruction processor 1140 is formed about a backplane bus 1141. An image CPU 1142 controls the backplane bus 1141 and it links the processor 1140 to the local area network 418. A memory module 1143 also connects to the backplane 1141 and it stores the data used to reconstruct images as will be described in more detail below. An array processor 1145 also connects to the backplane 1141 and it operates under the direction of the image CPU 1142 to perform the image reconstruction using the data in memory module 1143. The resulting image array 1146 is stored in memory module 1143 and is output by the image CPU 1142 to the operator work station 1115.

The function of the sorter 1134 is to receive the coincidence data packets and generate from them memory addresses for the efficient storage of the coincidence data. The set of all coincidence event rays that point in the same direction ($\theta$) and pass through the scanner's field of view is a complete projection, or "view". The distance (R) between a particular ray path in a projection view and the center of the field of view locates that ray within the view. As shown in FIG. 11, for example, an event 1160 occurs along a projection ray 1162 which is located in a view at the projection angle $\theta$ and the distance R. The sorter 1134 counts all of the events that occur on this projection ray (R,$\theta$) during the scan by sorting out the coincidence data packets that indicate an event at the two scintillator crystals lying on this projection ray. During an emission scan, the coincidence counts are organized in memory 1143 as a set of two-dimensional arrays, one for each axial image, and each having as one of its dimensions the projection angle $\theta$ and the other dimension the distance R. This $\theta$ by R map of the measured coincidence events is called a histogram, or more commonly the sinogram array 1148.

Coincidence events occur at random and the sorter 1134 quickly determines the $\theta$ and R values from the two scintillator crystal addresses in each coincidence data packet and increments the count of the corresponding sinogram array element. At the completion of the emission scan, the sinogram array 1148 stores the total number of annihilation events which occurred along each ray. The number of such annihilation events indicates the number of positron electron annihilation events that occurred along the ray (R,$\theta$) during the emission scan and within a few minutes hundreds of thousands of events are typically recorded. These numbers are used to reconstruct a tomographic image.

It can be appreciated that the quality of a PET image will depend to a great extent on the number of scintillation events that are allowed to accumulate in the sinogram 1148. The longer the scan continues, the larger the number of detected scintillation events and the higher the quality of the reconstructed image.

Image Reconstruction for PET Imaging System

Figure 12:
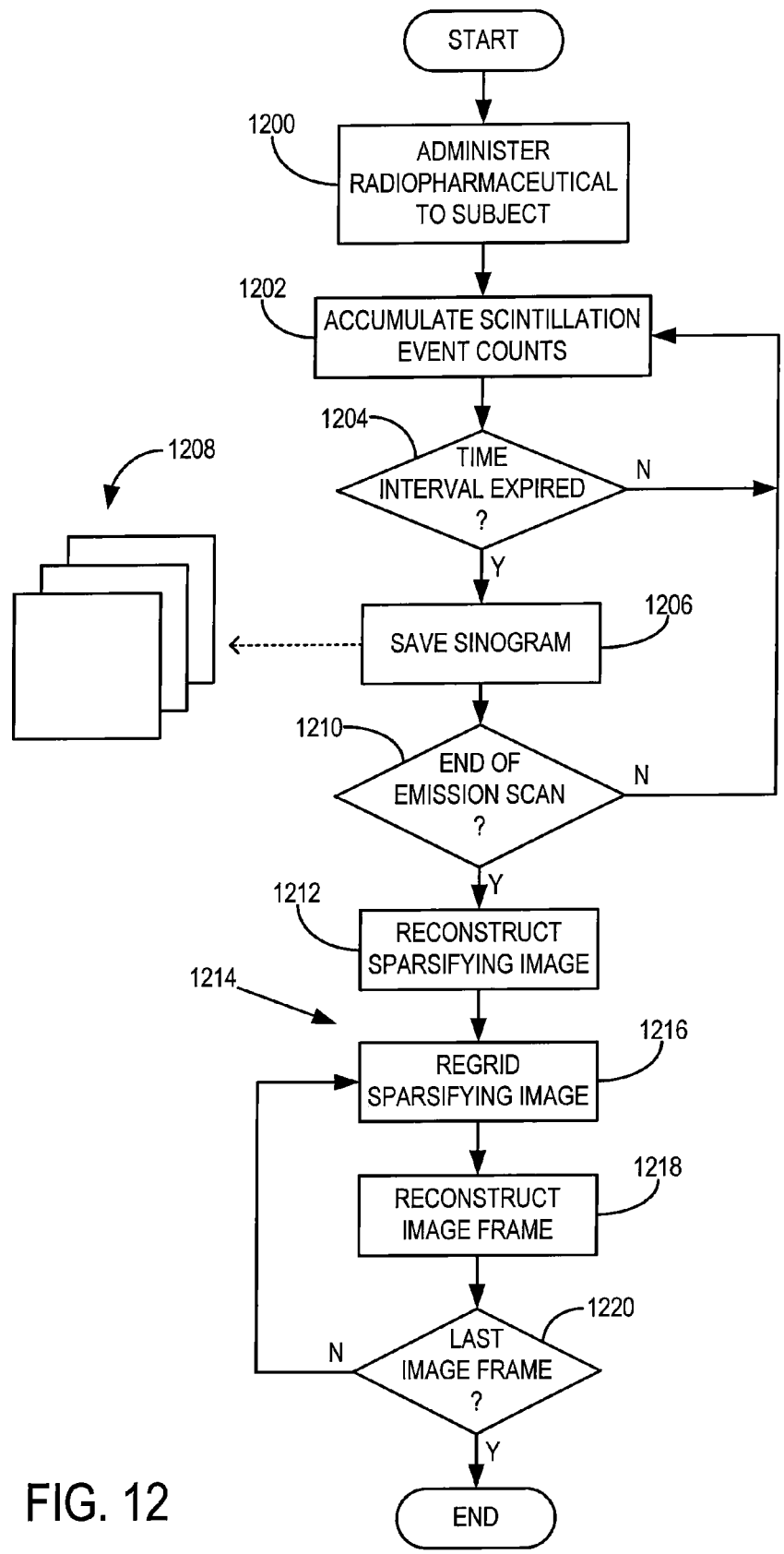
FIG. 12 is yet another embodiment of the invention using the PET scanner of FIG. 11.

Referring particularly to FIG. 12, the present invention may be employed by the PET scanner to perform a time-resolved emission scan. The emission scan begins as indicated at process block 1200 by injecting a radionuclide into the subject of the examination. The radionuclides most often employed in diagnostic imaging are fluorine-18 ($^{18}$F), carbon-11 ($^{11}$C), nitrogen-13 ($^{13}$N), and oxygen-15 ($^{15}$O). These are employed as radioactive tracers called "radiopharmaceuticals" by incorporating them into substances, such as glucose or carbon dioxide. The radiopharmaceuticals are injected in the patient and become involved in such processes as glucose metabolism, fatty acid metabolism and protein synthesis.

The subject is placed in the bore 1112 of the PET scanner and scintillation events are detected and counted as indicated at process block 1202. As described above, the scintillation events are detected, sorted and stored in sinogram 1148 as counts for each ray R in the projection views $\theta$. Events are counted and accumulated for a relatively short time interval as determined at decision block 1204. This time interval determines the time resolution of the emission scan and it may be, for example, one-tenth the duration of a conventional emission scan. As indicated at process block 1206, when the time interval expires the accumulated scintillation event counts are saved as a time interval sinogram 1208.

The emission scan continues and the accumulated sinogram count is saved after each time interval until the end of the scan is detected at decision block 1210. End of scan may be a preset time or a preset number of time intervals. In either case, a plurality of time interval sinograms 1208 will be produced during the emission scan and the last sinogram 1208 will store the total count for the entire emission scan. Each time interval sinogram 1208 is analogous to an image data set acquired with the MR and CT imaging systems described above.

The image reconstruction phase of the scan now begins, and during this phase an image frame indicative of the uptake of radiopharmaceutical at the end of each time interval is reconstructed. First, as indicated at process block 1212, a sparsifying image is reconstructed. This is a conventional backprojection reconstruction using the last sinogram 1208 saved during the emission scan. This contains the accumulated scintillation events for the entire emission scan and the image quality will be the best possible.

A loop is then entered at 1214 in which time resolved image frames are reconstructed using this sparsifying image. More specifically, as indicated at process block 1216 an iterative reconstruction of each stored time interval sinogram 1208 is performed. This iterative reconstruction is performed as described above in equation (3) by first regridding the recently reconstructed sparsifying image, as indicated in step 1216 and described above. This is a constrained minimization problem in which the accumulated scintillation count for each ray R in each view θ of the time interval sinogram 1208 is entered as the data vector s into equation (3). Additionally, and as described with reference to the other embodiments of the present invention, a difference data set is produced for each time interval sinogram 1208 by subtracting said time interval sinogram 1208 from the regridded sparsifying image data.

The image frame reconstruction process 1218 is repeated until image frames corresponding to each time interval sinogram 1208 is produced as detected at decision block 1220. As a result, a series of image frames are produced which indicate the uptake of the radiopharmaceutical at each time interval during the emission scan. By using the higher quality sparsifying image in the reconstruction, the image quality of each image frame is substantially improved over conventional images reconstructed using sinograms having low annihilation event counts.

In this PET scanner embodiment the sparsifying image is not formed using additional interleaved views acquired during the scan, but rather, by combining the data acquired at the same set of views during each of a plurality of time intervals during the scan. Sparsifying image quality is improved in this embodiment by increasing the SNR of each view rather than increasing the number of views as in the prior embodiments described above. This same strategy can also be used in x-ray CT, for example, to reduce patient x-ray exposure without reducing image quality. In such an embodiment a series of image frames are acquired using the same set of projection angles in each image frame. However, the x-ray dose is lowered to reduce the exposure for the patient. The frame image SNR is retained by using the reconstruction method of the present invention with a sparsifying image produced by combining the low-dose attenuation measurements made during each image frame acquisition. Rather than adding coincidence event counts as in the PET scanner embodiment, the "combination" in this x-ray embodiment is the average of all the corresponding attenuation measurements in acquired frame images.

This same image reconstruction strategy can be used in reconstructing images acquired with single photon emission computed tomography (SPECT) systems. As with PET scanners, SPECT systems accumulate counts of detected photons emitted from the subject along different ray paths. During a scan a gamma camera is moved slowly to accumulate counts at different view angles. Using the present invention a series of image frames may be acquired by moving the gamma camera more quickly and repeatedly through the same series of view angles. A lower count is accumulated at each view angle so as not to increase total scan time, but the SNR of each reconstructed image frame is maintained using a sparsifying image that is formed by adding all the counts together for each view angle.

The present invention has been described in terms of one or more preferred embodiments, and it should be appreciated that many equivalents, alternatives, variations, and modifications, aside from those expressly stated, are possible and within the scope of the invention. It should be appreciated by those skilled in the art that there are many variations possible from the particular embodiments described above. For example, it should be appreciated by those skilled in the art that equations (3) and (4) can be modified such that a plurality of sparsifying images are employed to determine a corresponding plurality of correction images.

The invention claimed is:

1. A method for producing an image of a subject positioned in a field of view (FOV) of a medical imaging system, the steps comprising:
    a) acquiring, with the medical imaging system, a plurality of image data sets of the subject positioned in the FOV at a corresponding plurality of time frames;
    b) reconstructing a sparsifying image by combining the data from the plurality of acquired image data sets;
    c) producing a sparsifying image data set by transforming the sparsifying image reconstructed in step b);
    d) producing a difference image data set by subtracting the image data set acquired in a selected time frame from the sparsifying image data set produced in step d);
    e) iteratively reconstructing a correction image using the difference image data set produced in step d); and
    f) subtracting the correction image from the sparsifying image reconstructed in step b) to produce the image of the subject at the selected time frame.

2. The method as recited in claim 1 in which step c) includes regridding the sparsifying image to a sampling pattern of the image data set acquired at a selected time frame.

3. The method as recited in claim 1 in which step e) includes iteratively reconstructing the correction image using an iterative minimization having the form:

$$\min_{f_{corr}} \{\|s_{corr} - Ef_{corr}\|_p + \lambda\|\Psi f_{corr}\|_1\};$$

wherein:
   $f_{corr}$=the correction image;
   $s_{corr}$ the difference image data set;
   E=an encoding matrix that describes the relationship between the correction image, $f_{corr}$, and the difference image data set, $s_{corr}$;
   $\lambda$=a control parameter that balances a residual error and sparsification of the correction image $f_{corr}$;
   $\Psi$=a sparsifying transform;
   $f_s$=the sparsifying image reconstructed in step b); and
   $\|\ldots\|_p$ indicates p-norm.

4. The method as recited in claim 1 in which step e) includes iteratively reconstructing the correction image using an iterative minimization having the form:

$$\min_{f_{corr}} \{\|s_{corr} - Ef_{corr}\|_2^2 + \lambda\|\Psi f_{corr}\|_q^q\};$$

wherein:
   $f_{corr}$=the correction image;
   $s_{corr}$ the difference image data set;

E=an encoding matrix that describes the relationship between the correction image, $f_{corr}$, and the difference image data set, $s_{corr}$;

$\lambda$=a control parameter that balances a residual error and sparsification of the correction image $f_{corr}$;

$\Psi$=a sparsifying transform;

$f_s$=the sparsifying image reconstructed in step b); and $\|\ldots\|_q^q$ indicates a $q^{th}$ power of a q-norm.

5. The method as recited in claim 1 in which the medical imaging system is a magnetic resonance imaging (MRI) system and the image data sets acquired in step a) are interleaved k-space data sets.

6. The method as recited in claim 5 in which step a) includes performing a pulse sequence that samples k-space with radial k-space trajectories.

7. The method as recited in claim 5 in which step a) includes performing a pulse sequence that samples k-space with a spiral k-space trajectory.

8. The method as recited in claim 5 in which the MRI system includes a parallel radiofrequency (RF) receiver coil having a plurality of receiver coil elements and an image data set is acquired from each coil element at each of the plurality of time frames.

9. The method as recited in claim 8 in which step b) further includes producing an intermediate sparsifying image corresponding to each receiver coil element by multiplying the sparsifying image by a sensitivity profile of the corresponding receiver coil element.

10. The method as recited in claim 9 in which step c) includes producing a plurality of sparsifying image data sets by transforming the intermediate sparsifying images.

11. The method as recited in claim 10 in which step d) includes producing a plurality of difference image data sets by subtracting the image data sets acquired from the plurality of receiver coil elements at a selected time frame from the corresponding intermediate sparsifying images.

12. The method as recited in claim 11 in which step e) includes iteratively reconstructing a correction image using the plurality of difference image data sets produced in step d).

13. The method as recited in claim 1 in which the medical imaging system is an x-ray computed tomography (CT) imaging system and the image data sets acquired in step a) are interleaved Radon space data sets.

14. The method as recited in claim 1 in which the medical imaging system is a positron emission tomography (PET) imaging system and the image data sets acquired in step a) are a series of time-resolved sinograms.

15. The method as recited in claim 1 in which the medical imaging system is a single photon emission computed tomography (SPECT) imaging system and the image data sets acquired in step a) are a series of time-resolved sinograms.

16. The method as recited in claim 1 in which the plurality of image data sets acquired in step a) include undersampled image data sets.

17. The method as recited in claim 1 in which step b) includes reconstructing the sparsifying image with a HYPR-LR image reconstruction method.

18. A method for producing an image having improved quality as compared to a previously reconstructed image that forms a part of a series of previously reconstructed images of a subject, the steps comprising:
   a) transforming the series of previously reconstructed images to produce a plurality of corresponding image data sets;
   b) reconstructing a sparsifying image by combining data from the plurality of image data sets produced in step a);
   c) producing a sparsifying image data set by transforming the sparsifying image reconstructed in step b);
   d) producing a difference image data set by subtracting a selected image data set from the sparsifying image data set produced in step c);
   e) iteratively reconstructing a correction image using the difference image data set produced in step d); and
   f) subtracting the correction image from the sparsifying image reconstructed in step b) to produce the image of the subject that has improved quality as compared to the previously reconstructed images.

19. The method as recited in claim 18 in which step c) includes regridding the sparsifying image to a sampling pattern of a selected image data set.

20. The method as recited in claim 18 in which steps c)-f) are repeated for each image data set to improve the quality of each image in the series of images.

21. The method as recited in claim 18 in which step a) includes transforming each image in the series of images into Radon space.

22. The method as recited in claim 18 in which the series of images is a series of medical images produced with a medical imaging system.

23. The method as recited in claim 18 in which step b) includes reconstructing the sparsifying image with a HYPR-LR image reconstruction method.

* * * * *